United States Patent [19]

Cucuzza et al.

[11] Patent Number: 5,026,450
[45] Date of Patent: Jun. 25, 1991

[54] METHOD OF APPLYING ADHESIVE TO THE WAIST ELASTIC MATERIAL OF DISPOSABLE GARMENTS

[75] Inventors: Carl C. Cucuzza, Loganville; John M. Raterman; John P. Keuter, both of Lawrenceville, all of Ga.

[73] Assignee: Nordson Corporation, Westlake, Ohio

[21] Appl. No.: 421,614

[22] Filed: Oct. 13, 1989

[51] Int. Cl.$^5$ .................. B29C 47/00; B32B 31/04
[52] U.S. Cl. .................. 156/244.11; 156/85; 156/164; 156/244.18; 156/244.21; 156/256; 156/265
[58] Field of Search ............ 156/85, 164, 160, 244.11, 156/244.18, 244.21, 256, 265, 519, 552

[56] References Cited

U.S. PATENT DOCUMENTS

| 721,900 | 3/1903 | Lassoe et al. . |
|---|---|---|
| 2,626,424 | 1/1953 | Hawthorne, Jr. . |
| 3,053,461 | 9/1962 | Inglis . |
| 3,096,225 | 7/1963 | Carr et al. . |
| 3,152,923 | 10/1964 | Marshall et al. . |
| 3,690,518 | 9/1972 | Baker et al. . |
| 3,764,069 | 10/1973 | Runstadler, Jr. et al. . |
| 3,787,265 | 1/1974 | McGinnis et al. . |
| 3,825,379 | 7/1974 | Lohkamp et al. . |
| 3,841,567 | 10/1974 | Drozek et al. . |
| 4,031,854 | 6/1977 | Sprague, Jr. . |
| 4,081,301 | 3/1978 | Buell . |
| 4,128,667 | 12/1978 | Timson . |
| 4,159,199 | 6/1979 | Levecque et al. . |
| 4,185,981 | 1/1980 | Ohsato et al. . |
| 4,211,736 | 7/1980 | Bradt . |
| 4,219,157 | 8/1980 | Binoche . |
| 4,253,461 | 3/1981 | Strickland et al. . |
| 4,397,704 | 8/1983 | Frick .................. 156/552 |
| 4,411,389 | 10/1983 | Harrison . |
| 4,704,116 | 11/1987 | Enloe . |
| 4,711,683 | 12/1987 | Merkatoris .................. 156/164 |
| 4,738,677 | 4/1988 | Foreman . |
| 4,785,996 | 11/1988 | Ziecker et al. . |
| 4,795,510 | 1/1989 | Wittrock et al. . |
| 4,815,660 | 3/1989 | Boger . |
| 4,846,827 | 7/1989 | Sallee et al. . |
| 4,891,249 | 1/1990 | McIntyre .................. 427/421 |

FOREIGN PATENT DOCUMENTS

| 8534594 | 3/1986 | Fed. Rep. of Germany . |
|---|---|---|
| 1109198 | 8/1984 | U.S.S.R. . |
| 1240465 | 6/1986 | U.S.S.R. . |

OTHER PUBLICATIONS

Nordson Corporation Technical Publication 43-1-11, issued Mar. 1981, Amherst, Ohio.

Primary Examiner—Caleb Weston
Attorney, Agent, or Firm—Wood, Herron & Evans

[57] ABSTRACT

A method of applying adhesive to the heat shrinkable, waist elastic member of a disposable garment, and for attaching the elastic member to the backing sheet of the gartment, comprises extruding an adhesive bead from an adhesive dispenser and impacting the bead with jets of air directed substantially tangent to the periphery thereof to form an elongated adhesive fiber and to impart a twisting motion to the adhesive fiber. The adhesive fiber is deposited in a spiral pattern onto the heat shrinkable elastic member, preferably at an application temperature which substantially reduces activation of the heat shrinkable elastic member. The elastic member is cut into individual strips which are adhered at longitudinally spaced locations to the material forming the backing sheet of the disposable garment.

4 Claims, 1 Drawing Sheet

METHOD OF APPLYING ADHESIVE TO THE WAIST ELASTIC MATERIAL OF DISPOSABLE GARMENTS

FIELD OF THE INVENTION

This invention relates to the manufacture of disposable garments, and, more particularly, to an in-line method of applying adhesive to a strip of elastic material forming the waist elastic members of a disposable garment.

BACKGROUND OF THE INVENTION

Disposable absorbent garments such as disposable diapers and adult incontinence briefs have met with widespread use to absorb and contain body exudates. Commercially available disposable diapers, for example, are unitary preshaped and prefolded garments which include a moisture-impervious backing sheet, a body contacting layer or liner and a moisture absorbent core therebetween. Elasticized leg openings are formed at the sides of the diaper and elasticized front and back waist sections are formed at the ends of the diaper to improve the comfort of the garment and its ability to contain waste material.

One step in the process for forming disposable garments such as disposable diapers involves the attachment of strips of elastic material at longitudinally spaced locations along a moving sheet or web of the polyethylene material which forms the backing sheet of the disposable garment. Currently, an endless strip of elastic material is unwound from a roll and moved in a direction transverse to the path of a moving sheet of the polyethylene material. An adhesive dispenser applies one or two extruded beads, or a continuous coating, of hot melt thermoplastic adhesive to the elastic material which is then moved from the adhesive dispenser to a cutting station where it is cut lengthwise to form individual strips. These individual strips of elastic material are then attached at longitudinally spaced locations along the moving polyethylene material which form the front and back waist sections of the finished disposable garment. After the elastic strips are attached to the polyethylene backing sheet, further process steps are employed to attach the other layers of the diaper to form the finished garment.

In most methods, the elastic material utilized to form the waist elastic member of the disposable garment is a heat shrinkable material, which, under the application of sufficient heat, shrinks or shortens in length. Because this heat shrinkable elastic material is secured to the polyethylene backing sheet of the disposable garment, it forms gathers or pleats in the polyethylene material upon shrinkage. These gathers improve the fit of the garment on the wearer and aid in resisting the passage of body exudates out of the garment.

A number of problems have been encountered in the method described above for attaching heat shrinkable elastic material at the waist portions of disposable garments. As mentioned above, the elastic material utilized in such application is heat shrinkable so that gathers can be formed at the waist portions of the finished garment. It has been found that the application of relatively thick, extruded beads of adhesive or a continuous coating of adhesive onto this heat shrinkable elastic material can cause such material to prematurely activate or shrink. This is because thick extruded beads or a continuous coating of hot melt thermoplastic adhesive retain substantial specific heat after discharge from a dispensing device and upon application onto the heat shrinkable elastic material. As a result, a number of chill rollers must be employed downstream from the adhesive dispensers to reduce the temperature of the hot melt adhesive applied to the heat shrinkable elastic material and thus prevent such elastic material from activating or shrinking prematurely.

Another problem with the method described above is that the adhesive dispensers which apply hot melt adhesive to the heat shrinkable elastic material generally employ slot nozzles which contact the elastic material to obtain an adhesive pattern thereon which is uniform and sharply defined at the edges of the individual strips. This contact between the elastic material and slot nozzles tends to wear the slot nozzles requiring frequent replacement. Additionally, a mechanism must be provided to retract the nozzle from its contact position with the elastic material when the manufacturing operation is interrupted or terminated.

A further disadvantage of the method described above is that a relatively large quantity of adhesive is discharged in the form of extruded beads or a continuous coating from the adhesive dispensers utilized in such method. Moreover, the hot melt thermoplastic adhesive is highly viscous and can dull or clog the knife blades utilized to cut the elastic material to length in preparation for its attachment to the polyethylene backing sheet of the diaper. This leads to maintenance problems wherein the knife blades must either be replaced or cleaned of adhesive in order for the diaper manufacturing operation to proceed.

SUMMARY OF THE INVENTION

It is therefore among the objectives of this invention to provide a method of applying hot melt adhesive onto the heat shrinkable elastic material employed at the front and back waist portions of a disposable garment which reduces the quantity of adhesive applied to the elastic material, which substantially reduces the need for chill rollers, which reduces dulling and clogging of the knife blades used to cut the elastic material, which eliminates mechanisms for moving an adhesive dispenser relative to the elastic material and which increases the efficiency of the manufacturing operation while reducing costs.

These objectives are accomplished in the method of this invention wherein an adhesive dispenser is effective to deposit a thin, elongated adhesive fiber in a spiral pattern onto a moving length of heat shrinkable elastic material which is subsequently cut into individual strips and attached to the polyethylene backing sheet of a disposable garment. The adhesive dispenser extrudes a bead of hot melt thermoplastic material and impacts the outer periphery of such extruded bead with jets of air to attenuate and stretch the bead forming a relatively thin elongated adhesive fiber, and to impart a twisting or rotational motion to such elongated adhesive fiber. This rotating or swirling elongated adhesive fiber is then deposited in a spiral pattern onto the heat shrinkable elastic material which consists of a series of overlapping loops of the elongated fiber extending across the width of the strip of elastic material and longitudinally therealong as the elastic material moves with respect to the adhesive dispenser.

A number of advantages are obtained with the method of applying adhesive of this invention compared to the other methods described above. The elongated adhesive fiber produced by the adhesive dispenser herein is relatively thin compared to the extruded beads of hot melt adhesive applied by other dispensers. This thin elongated adhesive fiber tends to retain much less specific heat upon application to the heat shrinkable elastic material, and, as a result, the application temperature of the elongated adhesive fiber is sufficiently low to substantially reduce or prevent activation or shrinking of the strip of elastic material. This reduction in the application temperature of the hot melt adhesive provided by the method herein minimizes the number of chill rollers which must be placed downstream from the adhesive applicator to cool the adhesive, thus reducing the cost and difficulty of the adhesive application operation.

Another advantage of the method of this invention is a reduction in the quantity of adhesive which is required to obtain an acceptable bond between the heat shrinkable elastic material and the polyethylene backing sheet of the disposable garment. As mentioned above, the elongated adhesive fiber is applied to the elastic material in a spiral pattern consisting of longitudinally extending, overlapping loops of the thin, elongated adhesive fiber rather than a thick bead or continuous coating. This substantially reduces the amount of adhesive applied to the elastic material without sacrificing the bond strength required to affix the strips of elastic material to the polyethylene backing sheet.

The reduction in the quantity of adhesive applied to the elastic material also produces benefits when the material is subsequently cut to length. A lesser quantity of adhesive on the elastic material reduces wear or damage to the knife blades which cut such material, and also lessens the problem of clogging of the knife blades with adhesive as the cutting operation is performed. The expense of replacing or repairing worn knife blades is reduced, and the maintenance time associated with cleaning the blades during the manufacturing operation is also reduced.

A further advantage of this invention is that the adhesive dispenser is mounted in a fixed position above but not in contact with the moving strip of heat shrinkable elastic material. Because there is no contact between the nozzle of the adhesive dispenser and the elastic material, problems of wearing of the nozzle are eliminated and no mechanisms are required to move the adhesive dispenser toward or away from the elastic material when the manufacturing operation is interrupted and then resumed.

DESCRIPTION OF THE DRAWINGS

The structure, operation and advantages of the presently preferred embodiment of this invention will become further apparent upon consideration of the following description, taken in conjunction with the accompanying drawings, wherein.

DETAILED DESCRIPTION OF THE INVENTION

Figure 1:
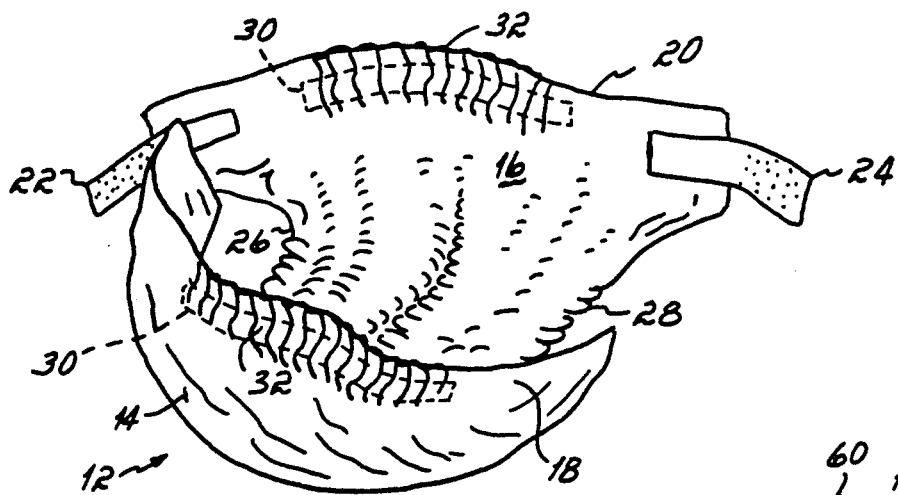
FIG. 1 is a schematic perspective view of a disposable garment having heat shrinkable elastic material at the front waist portion and back waist portion thereof.

Referring now to the FIGS., a method and apparatus is depicted for applying hot melt thermoplastic adhesive onto a length of elastic material 10 which is used in the formation of the waist elastic members of a disposable garment such as a disposable diaper 12. The disposable diaper 12 comprises a moisture-impervious, polyethylene backing sheet 14, a body contacting liner or layer 16, and a non-woven core or pad (not shown) therebetween. The diaper 12 is formed with a front waist section 18, a rear waist section 20 which mounts opposed tape tabs 22, 24, and elasticized leg openings 26, 28 on either side of the centerline of the diaper 12. The method of this invention is directed to applying hot melt thermoplastic adhesive to one side of the elastic material 10 which is adhered in individual strips 30 to both the front waist section 18 and rear waist section 20 of the diaper 12. The elastic material 10 forming the individual strips 30 is a heat sensitive or heat shrinkable material which, under the application of heat, shrinks or reduces in length to form gathers 32 in both the front and rear waist sections 18, 20 to improve the comfort and fit of the garment and its ability to contain waste material.

Figure 2:
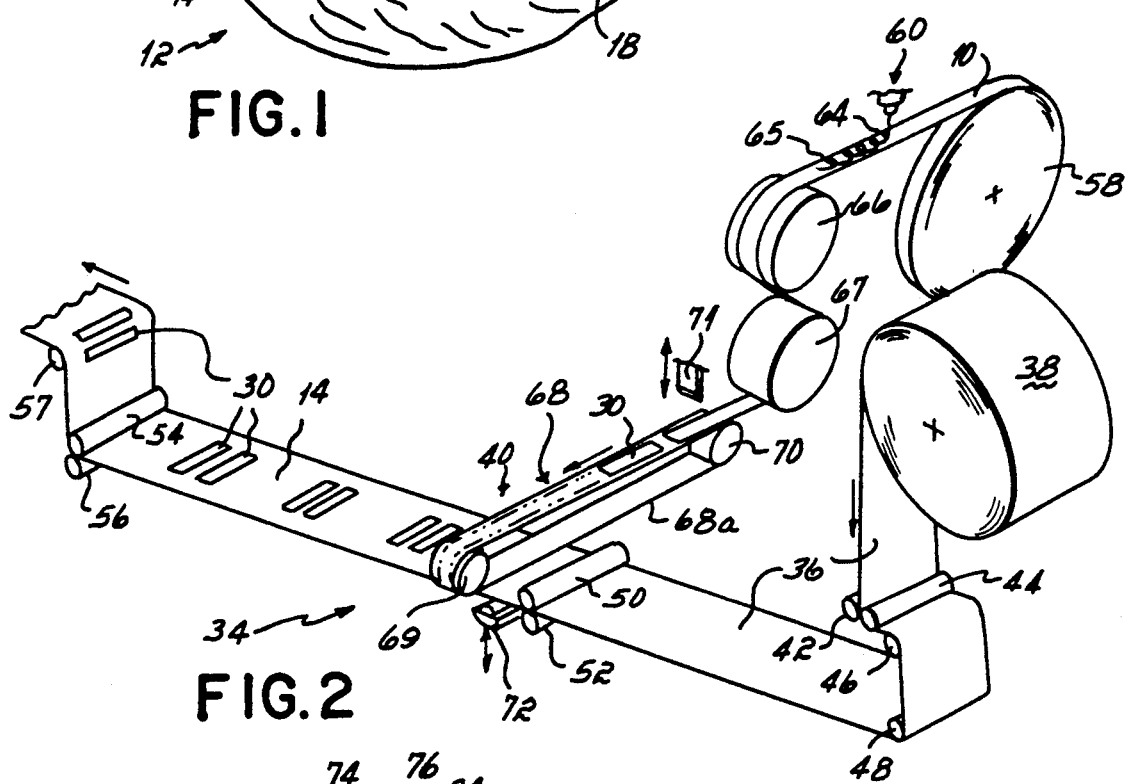
FIG. 2 is a schematic perspective view of an apparatus for adhering strips of heat shrinkable elastic material to the polyethylene backing sheet of a disposable garment.

Referring now to FIG. 2, a schematic view is illustrated of one form of an apparatus 34 for applying adhesive to one side of an endless length of elastic material 10 and for cutting such material 10 into individual strips 30 which are then attached at longitudinally spaced locations along a sheet or web of polyethylene material 36 used to form the backing sheet 14 of the disposable diaper 12. It should be understood that the apparatus 34 is illustrated in schematic form for purposes of describing the method of this invention, and no features of the apparatus per se form a part of this invention.

The apparatus 34 comprises structure for withdrawing the polyethylene material 36 from a roll 38 and feeding it past an attachment station 40 where individual lengths or strips 30 of elastic material 10 are adhered thereto at longitudinally spaced locations therealong. The polyethylene material 36 is fed through a pair of guide rollers 42, 44, over a dancer roller 46 and then around a third guide roller 48 to a pair of counterrotating nip rollers 50, 52 located immediately upstream from the attachment station 40. The sheet of polyethylene material 36 passes through the attachment station 40 where the individual strips 30 of elastic material 10 are adhered thereto, as discussed below, and then continues to a second pair of counterrotating nip rollers 54, 56 which feed the material 36 over a roller 57 to other stations (not shown) for further processing.

Referring to the right hand portion of FIG. 2, the structure for feeding the elastic material 10 in a direction transverse to the movement of the polyethylene material 36 is illustrated. The elastic material 10 is unwound from a roll 58 and directed beneath an adhesive dispenser 60 which applies an elongated adhesive fiber 64 in a spiral pattern 65 onto the elastic material 10 as described in detail below. The elastic material 10 continues from the adhesive dispenser 60 over a pair of rollers 66 and 67, one or both of which, depending upon the heat sensitivity of the elastic material 10, is a chill roller.

As schematically illustrated in FIG. 2, the elastic material 10 is directed from roller 67 onto a vacuum belt 68 located above the path of the polyethylene material 36. The vacuum belt 68 is movable on drive rollers 69 and 70 along a path substantially perpendicular to the travel of polyethylene material 36. A vertically movable cutter 71, illustrated schematically in FIG. 2, is operative to cut the elastic material 10 lengthwise to form individual strips 30 atop the upper run of the vacuum belt 68. These strips 30 are retained by the application of vacuum on belt 68 and are transferred by the belt 68 to a location immediately above the polyethylene material 36 along the lower run of belt 68a. A stomper 72 is positioned beneath the polyethylene material 36 which is effective to press the polyethylene material 36 against the vacuum belt 68 and the individual strips 30 it supports so that each of the strips 30 is adhered to the surface of the polyethylene material 36. As shown in FIG. 2, these individual strips 30 are longitudinally spaced along the polyethylene material 36 at locations which form the front and back waist sections 18, 20 of the finished disposable diaper 12.

Figure 3:
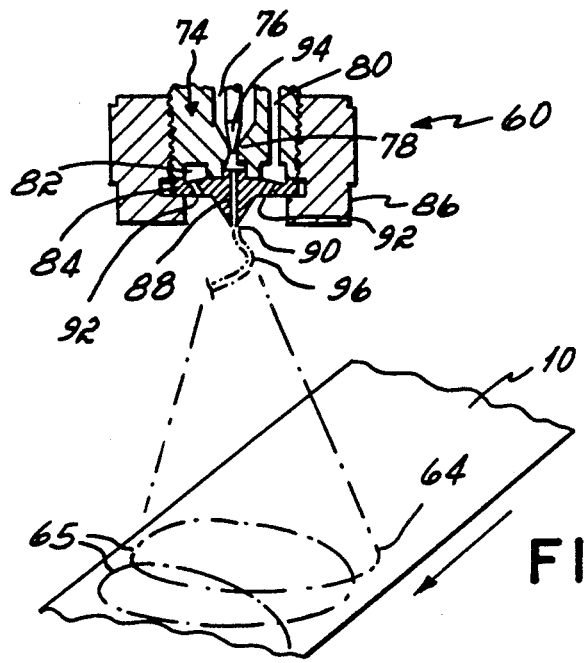
FIG. 3 is an enlarged front elevational view in partial cross-section of an adhesive dispensing device adapted for use with the apparatus of FIG. 2.

Referring now to FIGS. 2 and 3, the adhesive dispenser 60 utilized in the method of this invention is illustrated in further detail. In the presently preferred embodiment, this adhesive dispenser 60 is of the type disclosed in U.S. Pat. No. 4,785,996 to Ziecker et al, owned by the assignee of this invention, the disclosure of which is incorporated by reference in its entirety herein. As disclosed in detail in the Ziecker et al U.S. Pat. No. 4,785,996, the adhesive dispenser 60 mounts a nozzle 74 formed with an adhesive passageway 76 which communicates with a source of hot melt thermoplastic adhesive (not shown). The other end of the adhesive passageway 76 terminates at an adhesive discharge opening 78. An air delivery passageway 80 is formed in the nozzle 74 which is connected to an annular chamber 82 at the base of the nozzle 74. The air delivery passageway 80 is supplied with pressurized air from a source (not shown) for purposes to become apparent below.

A nozzle plate 84 is mounted by a cap 86 to the base of nozzle 74. The nozzle plate 84 is formed with a throughbore 88 having an inlet connected to the adhesive passageway 76 of nozzle 74 and a discharge outlet 90. A number of air jet bores 92 are formed in the nozzle plate 84 which are connected to the annular chamber 82 of the air delivery passageway 80 in nozzle 74. Each of the air jet bores 92 has a discharge outlet which is angled with respect to the longitudinal axis of the throughbore 88 in nozzle plate 84.

The operation of the adhesive dispenser 60 is as follows. Hot melt thermoplastic adhesive is introduced into the adhesive passageway 76 of the nozzle 74, and an air operated plunger 94, the lowermost end of which is illustrated in FIG. 3, is operative to permit the passage of the adhesive from the nozzle 74 into the throughbore 88 of the nozzle plate 84. The hot melt thermoplastic adhesive is extruded from the discharge outlet 90 of the nozzle plate 84 to form a relatively thick, extruded adhesive bead 96. At the same time, pressurized air is directed through the air delivery passageway 80 into the annular chamber 82 to the air jet bores 92 formed in the nozzle plate 84. As discussed in detail in U.S. Pat. No. 4,785,996, the air jet bores 92 of the nozzle plate 84 are angled relative to the longitudinal axis of the throughbore 88 therein so that the jets of air flowing through the air jet bores 92 impact the extruded bead 96 substantially tangent to its outer periphery at a point below the discharge outlet 90 of the throughbore 88. The air jets ejected from the air jet bores 92 perform two functions. First, the air jets attenuate or stretch the extruded bead 96 to form the elongated adhesive fiber 64 for deposition onto the elastic material 10. Secondly, the air jets from the bores 92 impart a rotational or twisting motion to the elongated adhesive fiber 64 so that such fiber 64 is deposited in a well defined, compact spiral pattern 65 onto the elastic material 10.

As schematically illustrated in FIGS. 2 and 3, this spiral pattern 65 of the elongated adhesive fiber 64 comprises a series of longitudinally extending overlapping loops which cover only a portion of the total surface area of the elastic material 10. The overlapping loops preferably have a transverse dimension substantially equal to the width of the elastic material, which, by employing the adhesive dispenser 60 herein, can be accurately controlled. The thin, elongated adhesive fiber 64 has a relatively low application temperature when it reaches the elastic material 10, e.g., less than about 300° F., which substantially reduces activation or shrinkage of the elastic material 10 and thus significantly reduces the need for chill rollers downstream therefrom to cool the adhesive. Additionally, a relatively small quantity of hot melt thermoplastic adhesive is required to form the spiral pattern 65 on the elastic material 10, but an acceptable bond is obtained between the polyethylene material 36 and the individual strips 30 of elastic material 10. Moreover, because of the substantial spaces or areas along the width and length of the elastic material 10 which are left uncovered by the thin loops or spirals of the elongated adhesive fiber 64, the cutter 71 utilized to form the individual strips 30 of elastic material 10 is protected from rapid dulling, and clogging with adhesive, during the cutting operation of the individual strips 30.

While the invention has been described with reference to a preferred embodiment, it will be understood by those skilled in the art that various changes may be made and equivalents may be substituted for elements thereof without departing from the scope of this invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. A method of applying adhesive onto the heat shrinkable waist elastic member of a disposable garment, comprising:
   extruding an elastic bead from a dispensing device and directing the extruded adhesive bead toward the heat shrinkable waist elastic member;
   impacting the extruded adhesive bead with jets of air directed substantially tangent to the periphery thereof prior to contact with the heat shrinkable waist elastic member to form an elongated adhesive fiber and to impart a twisting motion to the adhesive fiber;
   depositing the elongated adhesive fiber in a spiral pattern onto the heat shrinkable waist elastic member at an application temperature which substantially reduces activation of the heat shrinkable waist elastic member.

2. The method of claim 1 in which said step of depositing the elongated adhesive fiber comprises depositing the elongated adhesive fiber in a spiral pattern consisting of overlapping loops extending longitudinally along the waist elastic member, each of the loops having a transverse dimension which is substantially equal to the width of the waist elastic member.

3. A method of attaching a heat shrinkable elastic member to the waist sections of a disposable garment, comprising:

extruding an adhesive bead from a dispensing device and directing the extruded adhesive bead toward the heat shrinkable elastic member;

impacting the extruded adhesive bead with pressurized air directed substantially tangent to the periphery thereof to form an elongated adhesive fiber and to impart a twisting motion to the elongated adhesive fiber;

depositing the elongated adhesive fiber in a spiral pattern onto the heat shrinkable elastic member at an application temperature which substantially reduces activation of the heat shrinkable elastic member;

cutting the elastic member into individual strips and effecting contact between the strips and a sheet of material forming the backing sheet of the disposable garment to adhere the strips at longitudinally spaced locations along the backing sheet where the waist sections of the disposable garment are formed.

4. The method of claim 3 in which said step of depositing the elongated adhesive fiber comprises depositing the elongated adhesive fiber in a spiral pattern consisting of overlapping loops extending longitudinally along said elastic member, each of said loops having a transverse dimension which is substantially equal to the width of said elastic member.

* * * * *

UNITED STATES PATENT AND TRADEMARK OFFICE
CERTIFICATE OF CORRECTION

PATENT NO. : 5,026,450
DATED : June 25, 1991
INVENTOR(S) : Carl C. Cucuzza et al It is certified that error appears in the above-identified patent and that said Letters Patent is hereby corrected as shown below:

In column 6, line 52, please delete "elastic" and insert --adhesive--.

Signed and Sealed this

Twenty-second Day of December, 1992

Attest:

DOUGLAS B. COMER

*Attesting Officer*     *Acting Commissioner of Patents and Trademarks*